US00PP33181P2

(12) United States Plant Patent
Hansen

(10) Patent No.: US PP33,181 P2
(45) Date of Patent: Jun. 22, 2021

(54) ***HIBISCUS* PLANT NAMED 'FRENCH VANILLA'**

(50) Latin Name: ***Hibiscus* hybrid (L.)**
Varietal Denomination: French Vanilla

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,411

(22) Filed: Jan. 19, 2021

(51) Int. Cl.
*A01H 6/60* (2018.01)
*A01H 5/00* (2018.01)

(52) U.S. Cl.
USPC ..... Plt./257

(58) Field of Classification Search
USPC ..... Plt./257
See application file for complete search history.

*Primary Examiner* — Annette H Para

(57) ABSTRACT

A new and distinct cultivar of winter-hardy, herbaceous, perennial, hybrid *Hibiscus* plant named 'French Vanilla' comprising a compact, upright, spreading, mounded habit of multiple, well-branched, basal stems producing flowers from the bottom to the top of the plant from late July to early September. Flowers have overlapping, moderately-rippled petals opening creamy-yellow with slightly darker veins and dark red shiny eye with leading margin folded underneath giving flowers extra strength and resistance to wind damage. The flower buds open at the apex one to two days prior to the flower opening up flat, and the petals in the bud stage are greenish-yellow. The foliage is typically three-lobed, and rich olive-green with greyed-purple coloration when young.

2 Drawing Sheets

Botanical classification: *Hibiscus* hybrid (L.).
Variety denomination: 'French Vanilla'.

STATEMENT REGARDING PRIOR DISCLOSURES UNDER 37 CFR 1.77(B)(6)

The first non-enabling disclosure was a brief description and photograph of the new plant on Dec. 1, 2019 on the website operated by Walters Gardens, Inc. The first disclosure, in the form of a sale, was made by Walters Gardens, Inc. on Mar. 20, 2020. Walters Gardens, Inc. obtained the new plant and all information relating thereto, from the inventor. No plants of *Hibiscus* 'French Vanilla' have been sold, in this country or anywhere in the world, by any name, nor has any disclosure of the new plant been made more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'French Vanilla' hybridized under direction of the inventor Aug. 17, 2016 at a wholesale perennial nursery in Zeeland, Mich. The new plant is a self-pollination of the unreleased, proprietary hybrid known as 15-118-5 (not patented). Into the trial process the new plant was assigned the breeder code labeled 16-58-2. The parent has a complex mixture of species in them, comprising the species: *moscheutos* and *coccineus*.

*Hibiscus* 'French Vanilla' was first asexually propagated in late summer of 2018 by sterile shoot-tip tissue culture and later by shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'French Vanilla' differs from its parents as well as all other hardy herbaceous *Hibiscus* known to the applicant in many traits. The most similar *Hibiscus* cultivars known to the applicant are: 'Old Yella' U.S. Plant Pat. No. 13,630, 'New Old Yella' U.S. Plant Pat. No. 23,698, 'Creme Brulee' U.S. Plant Pat. No. 27,556 and 'Crown Jewels' U.S. Plant Pat. No. 11,857. 'Old Yella' has a taller and more open habit, the foliage is ovate and much lighter green, and the flower color is a lighter yellow. 'New Old Yella' has a larger habit with lighter green, smaller foliage with rounded bases, the flower petals are narrower, less imbricate, without the leading edge folded under, the center eye is smaller and lighter reddish color and the flower buds are not open at the apex days prior to opening flat. 'Crème Brulee' has a less branched habit, more purple-colored foliage, flowers with smaller eyes of lighter reddish color, petals without leading edges folded under and bud apices not opening slightly days prior to opening flat. 'French Vanilla' has more rippled flower petals than all of the above comparison plants. 'Crown Jewels' has a slightly taller and broader habit, and the flower color is more white.

The parent plant is less compact in habit, the foliage lighter green and the flowers lighter creamy yellow.

*Hibiscus* 'French Vanilla' is a unique hardy herbaceous *Hibiscus* with the following combined traits:

1. Winter-hardy compact perennial with upright, spreading, mounded habit of multiple, well-branched, basal stems;
2. Many rotate flowers opening creamy-yellow and becoming creamy-white with intense sun and high temperatures;

3. Petals are overlapping and moderately rippled with the leading edge folded underneath giving extra strength and resistance to wind damage;
4. Flowers produced over a long period from late July to mid-September;
5. Flower petals frequently open at bud apex one to two days prior to opening flat and are a greenish-yellow;
6. Primarily three-lobed foliage of rich olive-green with greyed-purple color when young.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plants in the photographs are from a three-year-old plant in an outdoor trial garden in Zeeland, Mich.

DETAILED BOTANICAL DESCRIPTION

Figure 1:
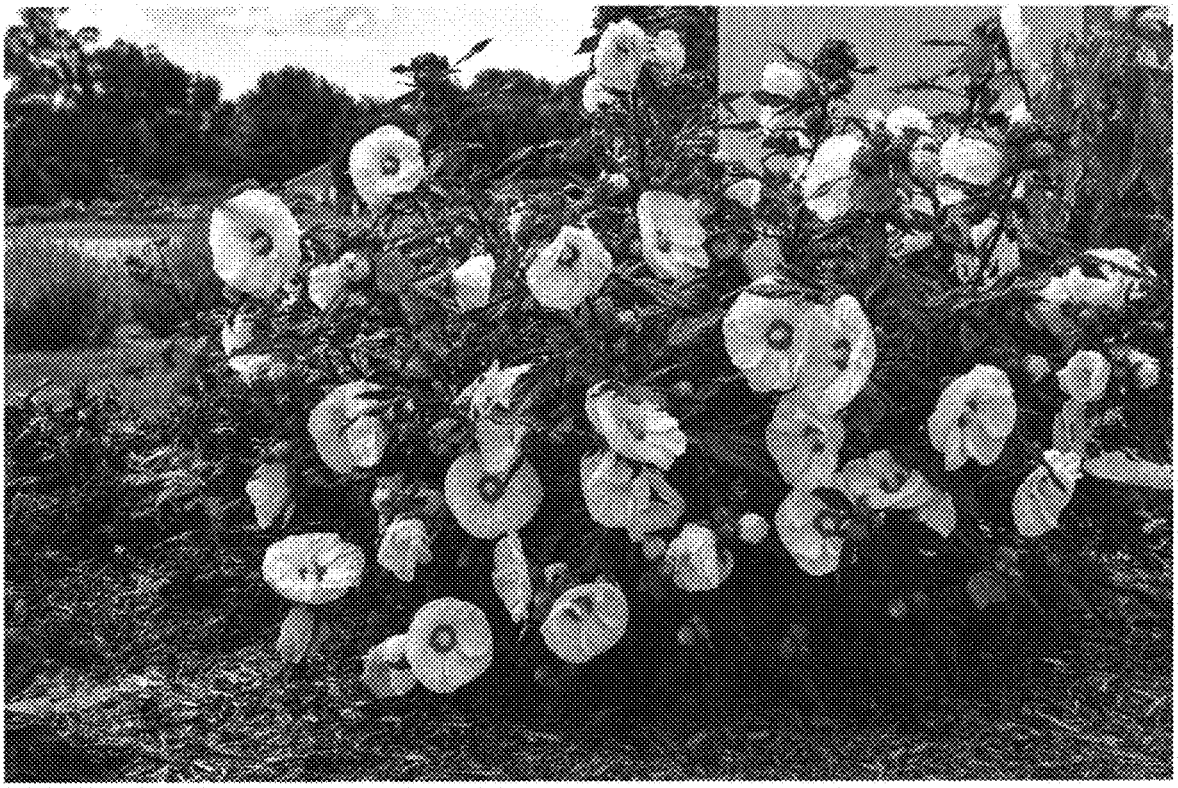
FIG. 1 shows the landscape habit of the new plant in full flower.
Figure 2:
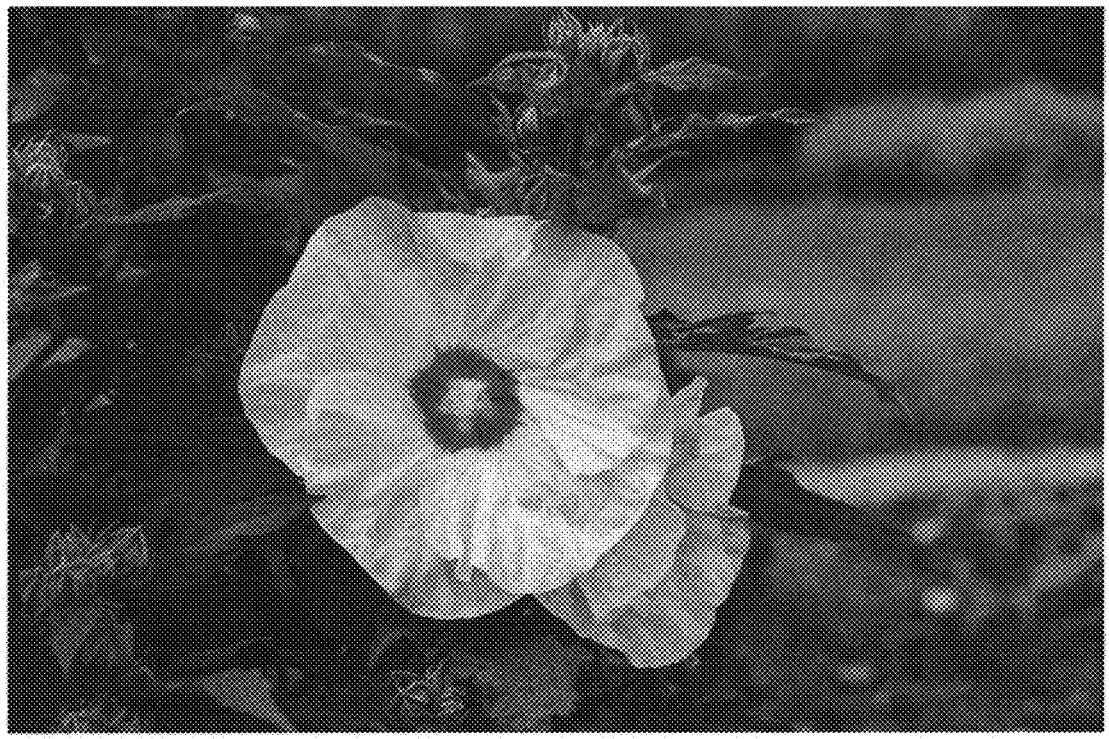
FIG. 2 shows a close-up of the flower.
Figure 3:
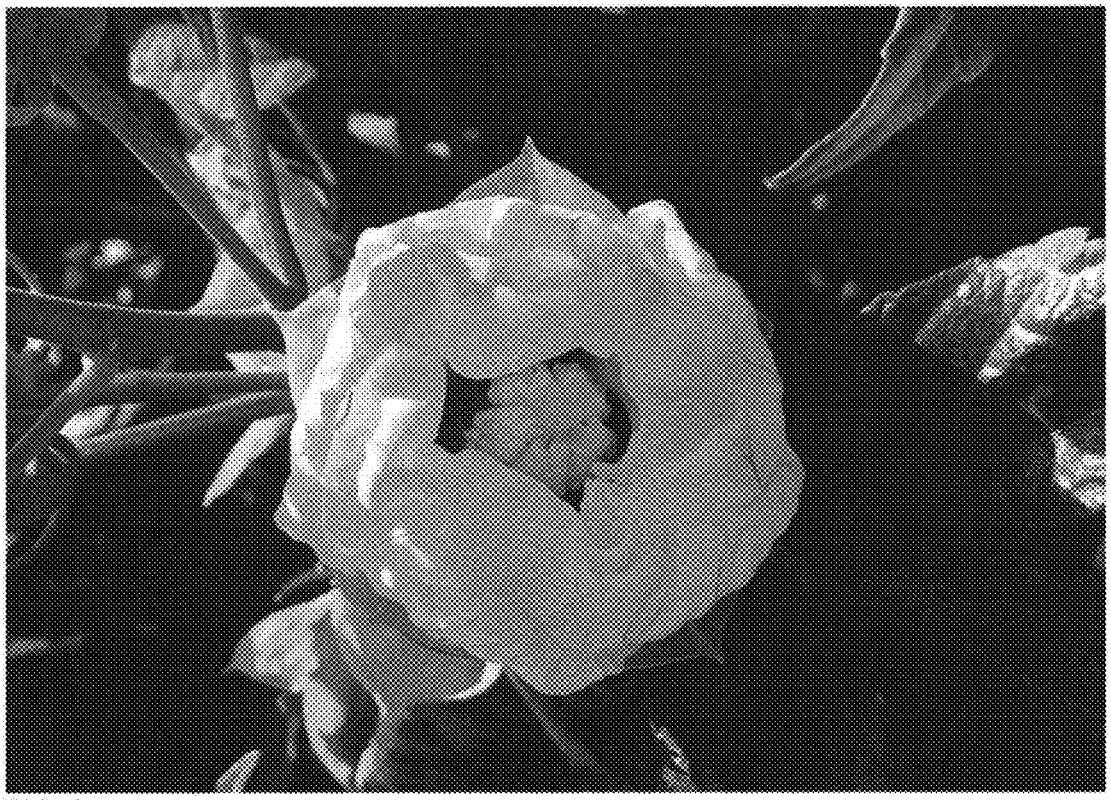
FIG. 3 shows the bud about a day before opening with the apex already open.

The following descriptions and color references are based on the 2015 edition of The Royal Horticultural Society Colour Chart except where common dictionary terms are used. The new plant, *Hibiscus* 'French Vanilla', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The female or seed parent is the unreleased, non-patented, proprietary *Hibiscus* known by the breeder code 15-118-5, the male or pollen parent is the same plant known by the breeder code 15-118-5;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2.2 cm diameter, fleshy; root color creamy yellow nearest RHS 161D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about five thick, upright, heavily-branched stems producing an upright spreading mound to about 104.0 cm tall and about 142.0 cm wide; flowering from base to top of plant with up to about 21 flowers in the upper main stem and up to 94 flowers on the branches of a single stem.

*Stem*.—Terete, glabrous, glaucous; to about 104.0 cm tall and about 3.8 cm diameter at base, average about 98.0 cm tall and about 2.8 cm diameter at base.

*Stem color*.—Proximal main stems nearest RHS 146A with lenticular marks of nearest RHS 145C; distal main stems nearest RHS 183C.

*Lateral branches*.—To 28 per stem, average about 12 per stem; terete; glabrous; glaucous; to about 39.0 cm long and 1.0 cm diameter at base, smaller distally.

*Lateral branch color*.—Proximally nearest a blend between RHS 138D and RHS 192C; distally nearest RHS 183C.

*Internode*.—About 6 nodes per stem below branches and 21 below single flowers; average about 50 nodes per stem; internode length about 2.0 cm of unpinched plant.

*Internode color*.—Same as surrounding stem.

Foliage description: Typically tri-lobed, rarely penta-lobed; alternate; coarsely and irregularly crenate; apex and side lobes narrowly acute; base truncate to cordate; micro-puberulent abaxial and adaxial; moderately to deeply incised, to about 20.0 mm from petiole; adaxial and abaxial surfaces dull; leaf blades to about 19.0 cm long and about 13.5 cm across, average blade size 15.0 cm long and 10.1 cm wide; no fragrance detected;

*Foliage color*.—Young expanding leaves — adaxial variable nearest RHS 137B and RHS N187A, abaxial nearest RHS 191B; mature leaves — adaxial nearest RHS NN137A, abaxial between RHS 148B and RHS 194A.

*Veins*.—Palmate; dull adaxial and abaxial; slightly applanate adaxial, costate on abaxial.

*Vein color*.—Adaxial nearest RHS 182A in basal main veins RHS 185C distally nearest RHS 148C, abaxial between RHS 160B and RHS 162B distally moderately blushed with nearest RHS 182B.

*Petioles*.—Applanate adaxial to abaxial, asperous adaxial and abaxial; glabrous; to about 8.0 cm long and 5.0 mm diameter at base, average about 6.2 cm long and 4.0 mm wide at base.

*Petiole color*.—Young and mature adaxial nearest RHS 146D blushed heavily with RHS 187B in high light; abaxial nearest RHS 146D moderately maculate to blushed with nearest RHS 187B distally in regions of high light.

Flower description: Complete; actinomophic; mostly outward facing; rotate; to about 16.0 cm across and 5.5 cm deep, decreasing distally; with a reddish center eye about 4.2 cm across;

*Buds one day prior to opening flat*.—Ellipsoidal with rounded apex and petals frequently open about 1.0 to 1.5 cm, and bluntly truncate base; sepals proximally adpressed to petals and distally flaring; to about 5.5 cm long and about 4.0 cm diameter in middle; petals not tightly closed at apices, open about 1.0 to 2.0 cm up to two days prior to petals opening flat.

*Bud color one day prior to anthesis*.—Exposed petal color nearest RHS 2D and calyx nearest RHS 146C.

*Epicalyx*.—Typically ten per flower; linear; margin entire, glabrous; dull surface abaxial and adaxial; sharply acute apex and truncate base, arcuate upwards near apex; about 2.3 cm long and about 3.0 mm wide at base.

*Epicalyx color*.—Adaxial nearest RHS 146C, and abaxial nearest RHS 146A.

*Calyx*.—Campanulate, form star-shaped hypanthium; to about 1.5 cm deep and 5.5 cm wide at apices.

*Sepals*.—Five, acute to apiculate apex; glabrous; margin entire, edentate; abaxial and adaxial surfaces matte; about 3.2 cm long, about 2.3 cm wide at slightly distal to fusion, fused in basal 1.5 cm.

*Sepal color*.—Adaxial nearest RHS 146C with veins of nearest RHS 146D; abaxial nearest RHS 146C without obvious veins.

*Inflorescence*.—Solitary, up to 115 per branched stem without pinching; nearly flat face; mostly outwardly facing.

*Flower lastingness*.—Persist for one to two days; effective for at least 6 weeks beginning late July.

*Flower fragrance*.—No detectable fragrance.

*Petals*.—Five; glabrous adaxial and abaxial; adaxial eye zone lustrous, remaining distal adaxial portion and entire abaxial matte; adnate to the androecium to form a column, leading edge (inside) frequently folded under between 3.0 to 10.0 mm; imbricate to about 100% overlapping at widest part (petals overlapping 100% to the petals on either side); undulation moderate; palmately veined, primary veins impressed on adaxial and slightly costate abaxial; surface moderately rippled; apex rounded with distinct basal claw and limb; margins entire, edentate.

*Petal size*.—Average about 12.3 cm across and about 8.2 cm long, claw base about 8.0 mm across (smaller in later part of flowering season); reddish eye extending about 2.1 cm from base with reddish midrib extending distally 9.0 mm beyond eye and secondary veins extending 5.0 mm beyond eye.

*Petal color*.—Adaxial distal portion nearest a blend between RHS 4D and RHS 155A, the proximal 3.0 mm next to column nearest RHS a blend between RHS 4D and RHS 155A, the reddish eye portion nearest RHS 59C and radiating veins between RHS 58A and RHS 58B.

*Gynoecium*.—Single; partially enclosed in column. Staminal column: glabrous and lustrous; about 2.4 cm long and about 13.0 mm across at base; with pistil exserted about 8.0 mm above top of column. Column color: without antnocyanins, nearest RHS NN155D. Style: cylindrical; nearly completely enclosed in column; micro-puberulent in region above staminal column, glabrous within column; about 3.2 cm long, penta-furcate in about distal 5.0 mm, branch diameter about 1.0 mm; color nearest RHS 4D. Stigma: typically five; globose, puberulent, about 3.0 mm in diameter and 1.0 mm tall; color RHS 4C. Ovary: superior; globose, longitudinally grooved; rounded to broadly acute apex and flat truncate base; about 6.0 mm across at base and about 7.0 mm tall; acute apex; color nearest RHS 146D.

*Androecium*.—Numerous, approximately 80 to 100. Filaments: terete; lustrous and sparsely puberulent; arcuate toward stigma; covering almost entire column; to about 3.0 mm long and about 0.5 mm diameter; color nearest RHS 155D. Anthers: oblong ellipsoidal; basifixed; longitudinal; about 2.0 mm long and 1.0 mm across and about 0.8 mm thick; color nearest RHS 11C. Pollen: abundant, globose, less than 0.1 mm long; color nearest RHS 19D.

Pedicel: Terete, glabrous in distal portion and micro puberulent in proximal portion; glaucous; average length from base of sepal to abscission point about 2.0 cm long, from abscission point to stem node about 1.0 cm long; about 3.0 mm wide; longer on early flowers and decreasing in distal flowers;

Pedicel color: Nearest RHS 146C distal abscission point, and RHS 146C with light blush of nearest RHS 178C proximal abscission point;

Peduncle: Terete; glabrous: glaucous; to about 104.0 cm tall and about 3.8 cm diameter at base, average about 98.0 cm tall and about 2.8 cm diameter at base;

Stem color: Proximal main stems nearest RHS 146A with lenticular marks of nearest RHS 145C; distal main stems nearest RHS 183C;

Fruit and seed: Not yet observed, but not tested for sterility;

Resistance: *Hibiscus* 'French Vanilla' has not displayed any pest and disease susceptibility or resistance beyond that typical of hardy perennial *Hibiscus*.

Culture: The plant grows best with plenty of moisture. Hardiness at least from USDA zone 4 through 9.

I claim:

1. A new cultivar of hardy herbaceous perennial *Hibiscus* hybrid plant named 'French Vanilla' as herein illustrated and described.

* * * * *